(12) United States Patent
Nagatani et al.

(10) Patent No.: US 8,322,355 B2
(45) Date of Patent: Dec. 4, 2012

(54) NON-INSERTED NOZZLE FOR STERILIZING OR WASHING BOTTLE CONTAINER AND METHOD FOR STERILIZING OR WASHING INNER SURFACE OF BOTTLE CONTAINER

(75) Inventors: Nobuaki Nagatani, Yokohama (JP);
Takeshi Iwashita, Yokohama (JP);
Kenichi Kominami, Yokohama (JP);
Keita Nakamori, Yokohama (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 366 days.

(21) Appl. No.: 12/304,020

(22) PCT Filed: Jun. 9, 2006

(86) PCT No.: PCT/JP2006/311656
§ 371 (c)(1),
(2), (4) Date: Dec. 9, 2008

(87) PCT Pub. No.: WO2007/141882
PCT Pub. Date: Dec. 13, 2007

(65) Prior Publication Data
US 2010/0229894 A1    Sep. 16, 2010

(51) Int. Cl.
*B08B 9/34* (2006.01)
*B08B 9/28* (2006.01)
*B08B 9/093* (2006.01)

(52) U.S. Cl. ........................ 134/198; 134/135

(58) Field of Classification Search .............. 134/169 R, 134/198, 166 R, 167 R; 239/103, 120–122, 239/561, 543, 548, 556, 544, 558, 559, 560, 239/567, 589, 598
See application file for complete search history.

(56) References Cited

U.S. PATENT DOCUMENTS
5,419,348 A * 5/1995 Kuta .......................... 134/58 R FOREIGN PATENT DOCUMENTS
JP     6-121974 A     5/1994
JP     06121974 A  *  5/1994
JP  2005-170393 A    6/2005
(Continued)

OTHER PUBLICATIONS
Machine Translation of JP2005211779 A.*
(Continued)

*Primary Examiner* — Michael Kornakov
*Assistant Examiner* — Caitlin N Dunlap
(74) *Attorney, Agent, or Firm* — Westerman, Hattori, Daniels & Adrian, LLP

(57) ABSTRACT

A non-inserted nozzle for washing a container that can increase the washing efficiency, decrease the amount of washing fluid used, and shorten the washing time in sterilizing and washing a bottle container. The upper end surface of a non-inserted nozzle 8 serves as a liquid-receiving surface 10, and a retention wall 11 of a predetermined height is formed on the outer periphery of the liquid-receiving surface, thereby producing a retention recess. A plurality of nozzle holes 13 linked to a fluid channel of a nozzle stem 14 are provided obliquely so as to spread outwardly substantially in the central section of the liquid-receiving surface. The non-inserted nozzle 8 is disposed below the mouth of an inverted container 28 at a distance H from it and the sterilizing fluid or washing fluid is sprayed from below the mouth of the container, without inserting the nozzle into the container.

2 Claims, 5 Drawing Sheets

FOREIGN PATENT DOCUMENTS

| | | | |
|---|---|---|---|
| JP | 2005-211779 A | | 8/2005 |
| JP | 2005211779 A | * | 8/2005 |

OTHER PUBLICATIONS

Machine Translation of JP 06121974 A.*

Notification of Transmittal of Translation of the International Preliminary Report on Patentability (Form PCT/IB/338) of International Application No. PCT/JP2006/311656 mailed Jan. 22, 2009 with Forms PCT/IB/373 and PCT/ISA/237.

International Search Report of PCT/JP2006/311656, date of mailing Jul. 18, 2006.

* cited by examiner

Fig. 1-A
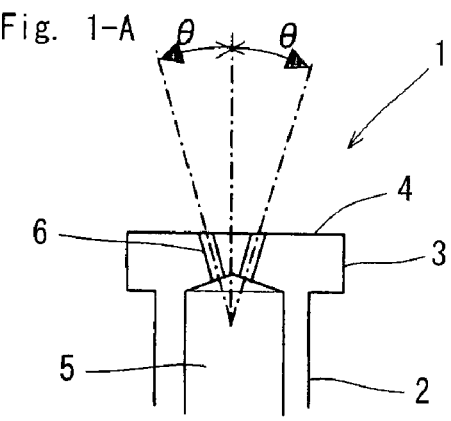
Fig. 1-B
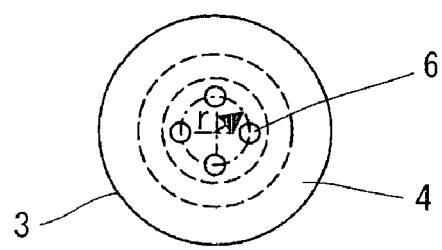
Fig. 2-A
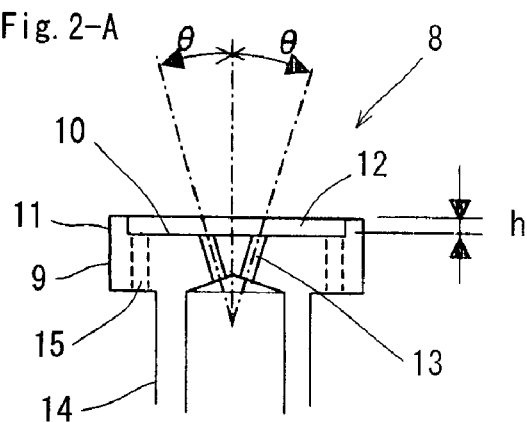
Fig. 2-B
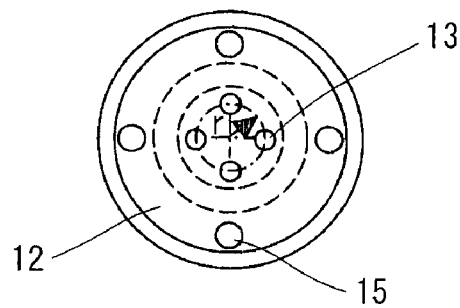

NON-INSERTED NOZZLE FOR STERILIZING OR WASHING BOTTLE CONTAINER AND METHOD FOR STERILIZING OR WASHING INNER SURFACE OF BOTTLE CONTAINER

TECHNICAL FIELD

The present invention relates to a non-inserted nozzle for sterilizing or washing a bottle container and to a method for sterilizing or washing the inner surface of a bottle container, and more particularly to a non-inserted nozzle for sterilizing or washing a bottle container (simply referred to hereinbelow as "container") with the object of reducing the amount of sterilizing fluid or washing fluid used and conducting efficient bottle sterilization or washing, and to a method for sterilizing or washing the inner surface of a container, in particular to a non-inserted nozzle and a method for washing the inner surface of a container that are more advantageous for washing after sterilization.

BACKGROUND ART

A method by which containers are sterilized in an inverted state by using a sterilizing liquid such as an aqueous solution of peracetic acid has been widely used for sterilizing bottle containers in an aseptic loading system. The sterilization effect of the inside of the container in this method due to wetting of the inner surface of the container by the sprayed sterilizing liquid, and in order to obtain good sterilization effect, the entire inner surface of the container has to be wetted uniformly with the sterilizing liquid. Furthermore, in the washing process performed after the sterilization process, the sterilizing liquid that has adhered to the entire inner surface of the container has to be washed down without leak. With the conventional method for washing inverted containers, a washing nozzle is inserted into the mouth of the container and a washing fluid (mainly, aseptic water) is sprayed therefrom. If the sprayed amount of the washing fluid is small, the ability to wet uniformly the entire inner surface of the bottle is lost and washing leak appears on the inner surface of the container. For this reason, a large quantity of the washing fluid has to be sprayed inside of the container. In particular, in the case of synthetic resin containers such as PET bottles, peaks and valleys of complex shape, such as reinforcing ribs, are present on the bottom and body section to increase the rigidity of container. Therefore, a large quantity of washing fluid has to be sprayed over a long period in order to wet uniformly the entire inner surface of the container, thereby hindering the transition to high-speed lines that has been urgently required in recent years. Furthermore, since a large quantity of washing fluid is required, it causes waste of the washing fluid and cost increase. In order to solve the above-described problems, the inventors have suggested a method and a fluid spraying nozzle by which the contact ratio of a washing fluid with the inner surface of a bottle is increased and washing is conducted with high efficiency in which a first spraying hole is formed in the center of a distal end section of a spraying nozzle that is to be inserted into the mouth of the inverted bottle and a second spraying hole is formed to be opened below the first spraying hole, the washing liquid sprayed from the two spraying holes toward the bottom section of the container flows down, and part of the liquid is stirred and pushed up by the washing fluid sprayed from the second spraying hole and scattered over the inner surface of the bottle (ref. Patent Document 1).

A method and nozzle for washing and sterilizing containers according to which a nozzle having a liquid receiving section is disposed below a container mouth and a liquid flow from a liquid ejection hole is caused to pass through a reflux flow that was retained in the liquid-receiving section, whereby the ejected liquid is caused to oscillate and the distal end of the liquid flow that collides with the inner surface of the container is constantly oscillated over the inner surface of the bottom section of the container, thereby increasing the contact ratio with the flow with the inner surface of the container, has also been suggested as a method for sterilizing or washing a container in which the container is held in an inverted state and a nozzle is not inserted into the container (ref. Patent Document 2).

Patent Document 1:
Japanese Patent Application Laid-open No. 2003-181404
Patent Document 2:
Japanese Patent Application Laid-open No. H6-121974

DISCLOSURE OF THE INVENTION

Problem to be Solved by the Invention

The former washing method and washing nozzle of the above-described conventional technologies had a higher washing efficiency than a method by which the inside of a container was washed by simply spraying a columnar flow of a washing fluid inside the container and made contribution to saving the washing fluid, but because the spraying nozzle was inserted into the container mouth to spray the washing fluid, a lifting device for inserting a spraying nozzle into the mouth of the container was required, the complexity and cost of the apparatus were increased, time had to be ensured for inserting the spraying nozzle into the container mouth and removing the nozzle therefrom, processing speed could not be increased, and because the spraying nozzle was frequently raised and lowered, problems requiring solution were associated with endurance, maintenance, and inspection of the apparatus. Furthermore, with simple spraying of the washing fluid, the ratio of washing fluid participated in wetting the inner surface of the container is small as compared with a large amount of required washing fluid and a problem requiring resolution is also associated with a large waste of the washing fluid. On the other hand, with the latter method the nozzle is not inserted into the container, the mechanism is simple, and the line speed is increased. However, because irregular oscillation of the atomized liquid flow are used to provide for uniform contact of the washing fluid with the inner surface of the container, there are intervals in which the washing liquid falls and periods in which the liquid does not fall on the bottom section of the container and the process lacks reliability. Similar problems are also encountered when the inner surface of the container is sterilized.

Accordingly, an object of the present invention is to provide a non-inserted nozzle for that served for washing or sterilizing container washing or sterilizing the inner surface of a container conveyed in an inverted state, the washing efficiency of washing fluid or sterilization efficiency of sterilizing fluid are increased, the amount of washing fluid or sterilizing fluid that is used can be reduced, and the washing time and sterilizing time can be shortened, and also to provide a method for sterilizing and washing the inner surface of a container that uses such nozzle.

Means for Solving Problem

The non-inserted nozzle for washing or sterilizing a container that resolves the above-described problems is a non-inserted nozzle for washing or sterilizing a container by spraying a washing fluid or sterilizing fluid, in a non-inserted state, into the container from below the container mouth to wash or sterilize the container in an inverted state thereof, the non-inserted nozzle comprising a hollow nozzle stem having a fluid channel formed inside thereof and a nozzle mouth provided at the top section of the hollow nozzle stem, in the nozzle mouth, the upper end surface serves as a liquid-receiving surface, and a plurality of nozzle holes linked to the fluid channel of the nozzle stem are formed obliquely at a predetermined angle substantially in the central section of the liquid-receiving surface.

It is preferred that from two to ten nozzle holes be formed with a predetermined spacing on a circle of a substantially central section of the liquid-receiving surface, the inclination angle θ of outward spread be 1 to 8°, and the nozzle hole diameter be 0.5 to 4.0 mm. For the nozzle holes to provide for efficient contact of the washing fluid sprayed from the nozzle holes with the inner surface of the container, it is preferred that the sprayed liquid fall in the vicinity of the corner portion of the bottom and body sections of the container and then flow along the inner surface of the bottom section and inner surface of the body section and it is preferred that at least two nozzle holes be provided on a circumference to wet the entire periphery of the inner surface. However, the entire periphery can be wetted without arranging the nozzle holes densely along the entire periphery. Accordingly, the sufficient number of nozzle holes is 10 or less. Furthermore, the inclination angle θ is preferably such that when the sprayed fluid passes through the mouth of the container, it passes with a certain clearance from the wall surface of the mouth of the container so as to avoid interference with the wall surface of the container mouth and so that the sprayed fluid then falls on the corner section of the container. The optimum inclination angle may be selected according to the size or shape of the container, but for bottles with an inner capacity of 200 to 2000 mL, this angle is preferably within a range of 1 to 8°. In this case, the sprayed liquid flow does not fall directly on the inner surface of the container mouth and the sprayed flow passes with a slight clearance from the inner wall of the mouth of the container. As a result, this flow interferes with part of the reflux flow that flows down along the inner peripheral surface of the bottle mouth, thereby pushing up the reflux flow. Furthermore, the diameter of nozzle holes in accordance with the present invention is less than that of the conventional sterilization nozzles or washing nozzles and washing or sterilization can be efficiently performed with a small amount of fluid by spraying the washing fluid or sterilizing fluid with good intensity. If the nozzle hole diameter is less than 0.5 mm, the flow rate is small and a juggling effect cannot be obtained, and if the nozzle hole diameter is more than 4 mm, the flow rate increases, the fluid remains inside the bottle, and the sprayed fluid does not reach the bottom section of the bottle.

The liquid-receiving surface preferably becomes the retention recess so as to retain the prescribed quantity of the reflux liquid discharged from the container during washing or sterilizing the container having the retention wall of the prescribed height formed on the outer periphery thereof. When the retention recess is provided, the reflux liquid that was discharged from the container is retained in the retention recess, whereby a juggling effect is demonstrated, the sterilizing or washing efficiency is increased, and the washing fluid or sterilizing fluid can be saved. It is preferred that one or a plurality of liquid discharge holes be formed on the inner side of the retention wall, so as to prevent the washing fluid or sterilizing fluid from remaining in the retention recess after the sterilizing and washing steps have been completed.

The method for sterilizing or washing an inner surface of a container in accordance with the present invention that resolves the above-described problems is a method for washing or sterilizing the inside of a container by spraying a washing fluid or sterilizing fluid inside the container conveyed in an inverted posture, wherein a non-inserted nozzle in which an upper end surface of a nozzle mouth serves as a liquid-receiving surface having a predetermined surface area and a plurality of nozzle holes are formed obliquely at a predetermined angle so as to spread outwardly almost in the central section of the liquid-receiving surface is disposed at a distance of 5 to 50 mm below the mouth of the container, the washing fluid or sterilizing fluid is sprayed from the non-inserted nozzle toward the inside of the container, and a reflux liquid that flows down from a mouth of the container after contacting with the inner surface of the container is received by the liquid-receiving surface.

In the method for sterilizing or washing the inner surface of a container, a retention wall of a predetermined height is formed on the outer periphery of the liquid-receiving surface of the non-inserted nozzle, a retention recess is formed such that a reflux liquid discharged from the container during container washing or sterilizing can be retained, the sterilizing fluid or washing fluid sprayed from the nozzle holes pushes up the reflux liquid retained in the retention recess, and the thickened sprayed liquid flow interferes with part of the reflux liquid flowing down in the container mouth, thereby producing a juggling effect, this method being especially preferred in the sterilizing step using warm water or washing step using aseptic water or warm water. For example, in the case containers to be filled with a contents liquid such as green tea, black tea, juices, sports beverages, near-water, and mineral water, warm water is employed as the sterilizing fluid, and in this case sterilization can be efficiently performed by employing the sterilization method of claim 5 or claim 6 in the sterilizing process. The temperature of warm water that can provide for efficient sterilization is 63 to 95° C. When warm water is used as a sterilizing fluid, the warm water serving as the sterilizing fluid also functions as a washing fluid. Therefore, the washing step following the sterilizing step is unnecessary. On the other hand, in the case of containers to be filled with contents liquid such as parched-barley tea, mixed tea, coffee, soup, and milk-containing beverages, a sterilizing liquid such as an aqueous solution of peracetic acid, aqueous solution of hydrogen peroxide, and an aqueous solution containing hypochlorous acid is employed.

Effect of the Invention

With the non-inserted nozzle in accordance with the present invention by forming and arranging the nozzle holes in the above-described manner, wetting of the inner surface of the container with the washing fluid or sterilizing fluid can be improved over that attained with the conventional spraying nozzles, the washing efficiency and sterilizing efficiency can be improved, and the washing fluid and sterilizing fluid can be saved. Furthermore, since the upper end surface of the nozzle mouth serves as a liquid-receiving surface, the reflux liquid that was obtained by spraying into the container, coming into contact with the inner wall surface of the container, flowing down, and discharging from the bottle mouth spreads over the liquid-receiving surface and flows out from the outer periphery of the liquid-receiving surface, but part of the reflux liquid directed toward the inner side of the liquid-receiving surface interferes with the sprayed fluid from the nozzle hole and is pushed up. As a result, the sprayed flow advances into the container in a state in which the diameter of the sprayed liquid flow is larger than that in the case of simple spraying from the nozzle holes. The sprayed liquid flow that advanced into the containers as a thickened flow interferes with part of the reflux liquid flowing down through the container mouth, thereby generating the juggling effect. Therefore, part of the reflux liquid flowing down from the container is supplied into the container again and can be make contribution to sterilization or washing and the washing fluid or sterilizing fluid can be saved accordingly. The juggling effect can be more effectively generated by forming a retention recess in the liquid-receiving surface. The juggling effect as referred to herein is an action of the sprayed liquid that pushes up and swings the reflux liquid up and down inside the bottle that is realized when a spraying nozzle is not inserted into the bottle, a liquid is sprayed from a plurality of nozzle holes onto the inner surface of the bottle, and the reflux liquid discharged from the bottle flows down along the bottle mouth and liquid-receiving surface of the nozzle, or is retained thereon. The larger is the juggling effect, the smaller is the amount of liquid required to provide the effective contact of the liquid with the entire inner surface of the bottle.

With the method for sterilizing and washing the inner surface of a container in accordance with the present invention, the non-inserted nozzle is disposed so as to be at a distance of 5 to 50 mm and below the mouth of a container conveyed in an inverted posture. Therefore, the washing fluid can be sprayed inside the container without inserting the spraying nozzle into the mouth of the container and removing it therefrom, it is not necessary to use a device for lifting the spraying nozzle, the sterilization time can be shortened, the number of drive components of the apparatus can be decreased, and the apparatus can be simplified and reduced in cost. Furthermore, since the upper end surface of the non-inserted nozzle serves as a liquid-receiving surface, the liquid discharged from the container can be discharged from a gap between the liquid-receiving surface and mouth end of the container. Moreover, due to the presence of the liquid-receiving surface, although the non-inserted nozzle is used, the juggling effect identical to that obtained with the inserted nozzle can be expected.

BRIEF DESCRIPTION OF THE DRAWINGS

FIG. 1 illustrates a non-inserted nozzle of an embodiment of the present invention; (a) is a cross-sectional view of the main portion of the non-inserted nozzle; (b) is a plan view thereof;

FIG. 2 illustrates a non-inserted nozzle of another embodiment of the present invention; (a) is a cross-sectional view of the main portion of the non-inserted nozzle; (b) is a plan view thereof;

EXPLANATIONS OF NUMERALS

Figure 3:
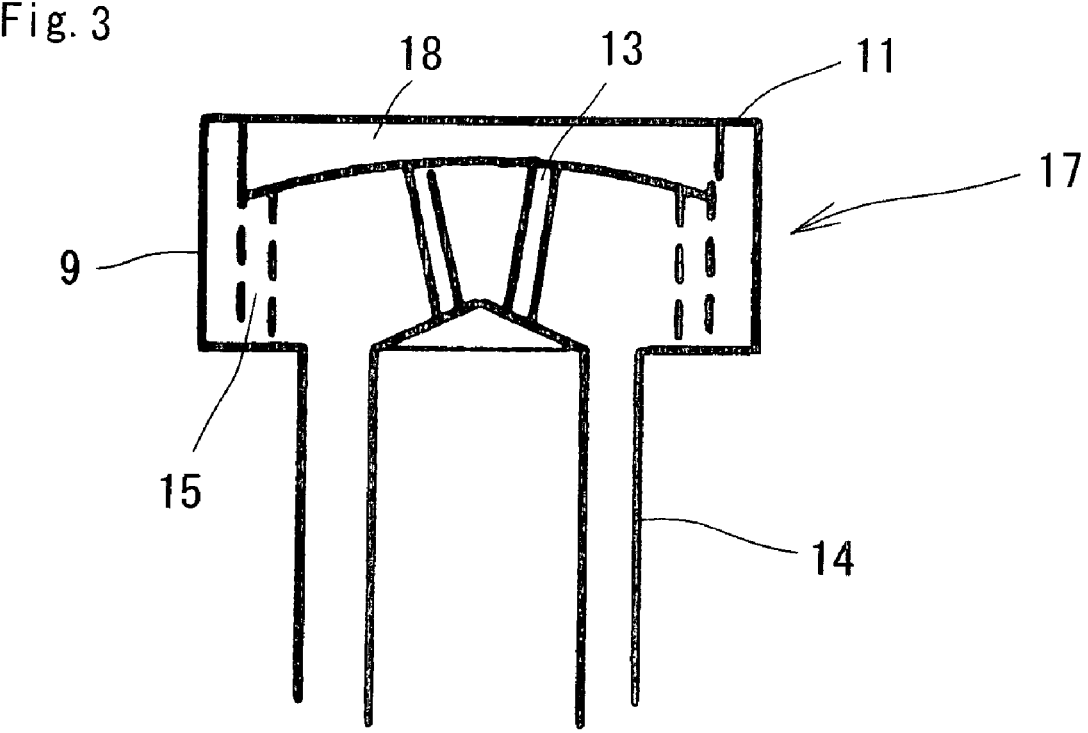
FIG. 3 is a cross-sectional view of the main portion of the non-inserted nozzle of yet another embodiment of the present invention.

| | |
|---|---|
| 1. 8. 17. | non-inserted nozzle |
| 2. 14. | nozzle stem |
| 3. 9. | nozzle mouth |
| 4. 10. | liquid-receiving surface |
| 5. | liquid channel |
| 6. 13. | nozzle hole |
| 11. | retention wall |
| 12. 18. | retention recess |
| 15. | liquid discharge hole |
| 28. | container |
| 30. | mouth of the container |
| 31. | lower end surface |
| 39. | aseptic chamber |
| 40. | partition wall |
| 41. | bottle supply turret |
| 42. | bottle reversion turret |
| 43. | preheating turret |
| 44. 45. 46. | sterilizing turret |
| 47. | sterilizing fluid discharge turret |
| 48. | transfer turret |
| 49. 51. | washing turret |
| 50. 52. | drain turret |

BEST MODE FOR CARRYING OUT THE INVENTION

FIG. 1 illustrates a nozzle mouth, which is the main portion of the non-inserted nozzle of the present embodiment. A non-inserted nozzle 1 of the present embodiment has a nozzle mouth 3 at the top section of a hollow nozzle stem 2, wherein the upper end surface of a predetermined diameter serves as a liquid-receiving surface 4 of a flat disk-like shape, and a plurality of nozzle holes 6 linked to a liquid channel 5 of the hollow nozzle stem 2 are formed in the vicinity of the central section of the nozzle mouth 3. The liquid channel 5 is linked to a sterilizing fluid supply source in the case of using the nozzle as a sterilizing nozzle via a pipe, not shown in the figure, and linked to a washing fluid supply source in the case of using the nozzle as a washing nozzle. Furthermore, in the case of atomizing and spraying the sterilizing fluid or the like from the non-inserted nozzle, the sterilizing fluid is pressurized and mixed with air in the non-inserted nozzle, supplied, and sprayed, whereby the sterilizing fluid can be atomized and jet sprayed. Furthermore, the diameter of the liquid-receiving surface 4 is preferably larger than or equal to that of the container mouth, but even if it is less than the bottle mouth diameter, increasing the amount of sterilizing liquid and the amount of washing water increases the amount of liquid sprayed from the container mouth, making it possible to cause interference with the reflux liquid inside the bottle mouth and to obtain the juggling effect.

In the example shown in the figure, a total of four nozzle holes 6 are formed equidistantly on a virtual circle with a diameter r less than the opening diameter of the mouth 30 of the container, which is sterilized and washed, in the vicinity of the central section of the mouth 3 of the nozzle, but this number can be appropriately selected within a range of 2 to 10. For example, when the container is a bottle with a quadrangular cross section, four nozzle holes are preferably provided with a 90° spacing to enable the spraying of fluid toward the corner sections, but this number is not limited to four. The inclination angle θ of the spray holes 6 depends on the mouth diameter of the container, but is within a range of 2° to 10°, more preferably within a range of 3° to 7° in the case of PET bottles (mouth diameter 28 mm) with a capacity of 200 to 2000 mL. The nozzle hole 6 preferably has a small diameter of 1 mm to 2 mm so that the washing fluid can be sprayed with good intensity. In order to satisfy two conditions: the sprayed fluid does not interfere with the inner peripheral surface of the mouth of the container and the sprayed washing fluid reaches the bottom surface of the container 28 and flows down in full contact with the inner peripheral surface of the container, it is preferred that a plurality of nozzle holes 6 be provided and inclined upward outwardly in the vicinity of the central section, as described hereinabove.

FIG. 2 illustrates a non-inserted nozzle of another embodiment of the present invention. In the non-inserted nozzle 8 of the present embodiment, similarly to the non-inserted nozzle 1 of the above-described embodiment, a liquid-receiving surface is provided on the upper end surface of the mouth 9 of the nozzle, but in the liquid-receiving surface 10 of the present embodiment, a retention wall 11 of a predetermined height "h" is formed on the outer periphery of the liquid-receiving surface, thereby providing a retention recess 12 such that the fluid discharged from the container during washing or sterilization of the container can be retained therein. Furthermore, a plurality of nozzle holes 13 are formed, according to the conditions identical to those of the above-described embodiment, in the retention recess 12. A liquid discharge hole 15 is formed in the retention recess 12 so as to be open on the outside of the outer peripheral section of the nozzle stem 14 in order to discharge rapidly the reflux liquid that was retained in the retention recess after the sterilization or washing has been completed. More than one liquid discharge hole 15 may be provided, by it is preferred that a plurality of liquid discharge holes be provided equidistantly to enable the uniform discharge of liquid from the liquid-retaining surface. The hole diameter has to be such as to ensure that the amount of liquid less than the discharged amount that flows down from the bottle mouth can be discharged, so that at least a fixed quantity of the reflux liquid can be retained in the retention recess 12 during sterilization or washing of the container. Furthermore, the height h of the retention wall 11, together with the size of the liquid discharge holes 15, regulate the amount of reflux liquid retained in the retention recess. If this height of wall 11 is too high, the amount of the retained liquid is increased and, the interference with the sprayed liquid is increased. So good discharge becomes impossible.

FIG. 3 shows a modification example of the non-inserted nozzle shown in FIG. 2. Components common with the non-inserted nozzle 8 are assigned with identical reference numerals, and only the difference between the two nozzles will be described below. The difference between the non-inserted nozzle 17 of the present embodiment and the non-inserted nozzle shown in FIG. 2 is in that the bottom of the retention recess 18 has a gradual spherical shape. By forming the liquid discharge holes 15 adjacently to the retention wall 11 in the deepest zone of the sphere, the reflux liquid retained in the retention recess can be rapidly discharged after completion of sterilization or washing.

Figure 6:
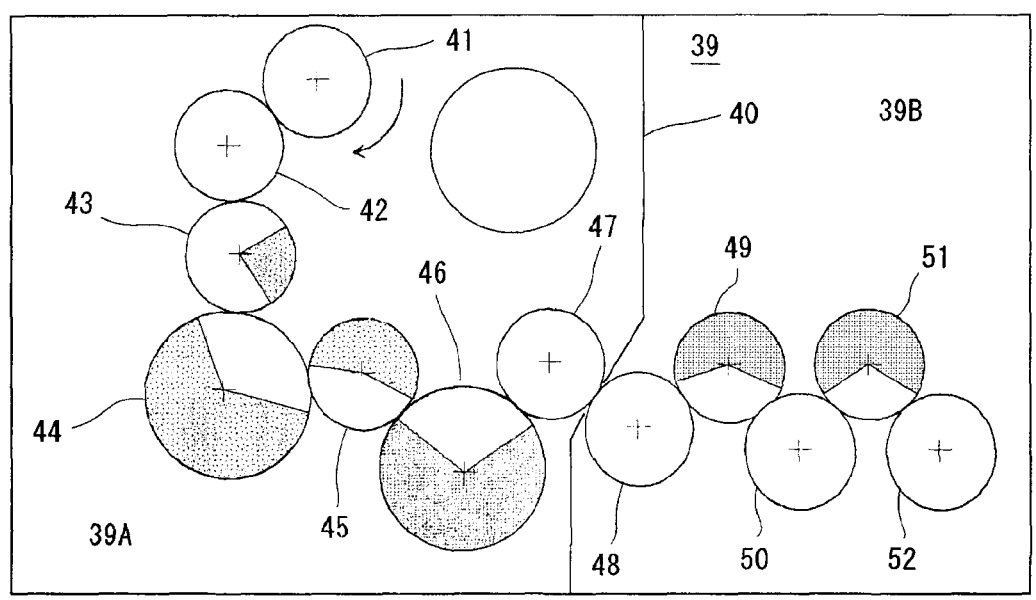
FIG. 6 is a schematic drawing illustrating the arrangement of a container sterilizing and washing apparatus for implementing the container sterilizing and washing method in accordance with the present invention.

An embodiment of the method for sterilizing and washing the inner surface of the container in accordance with the present invention by using the above-described non-inserted nozzle will be described below. The present invention is preferably applied to an apparatus for sterilizing and washing the inner surface of the container that comprises a large number of small turrets as shown in FIG. 6 described below, but the present invention can be also advantageously employed in a sterilizing and washing apparatus of the conventional configuration in which an inversion zone for turning containers upside down so that they assume an inverted state, a container sterilization zone and a drain zone for discharging the washing fluid are provided around one large-diameter turret.

Figure 4:
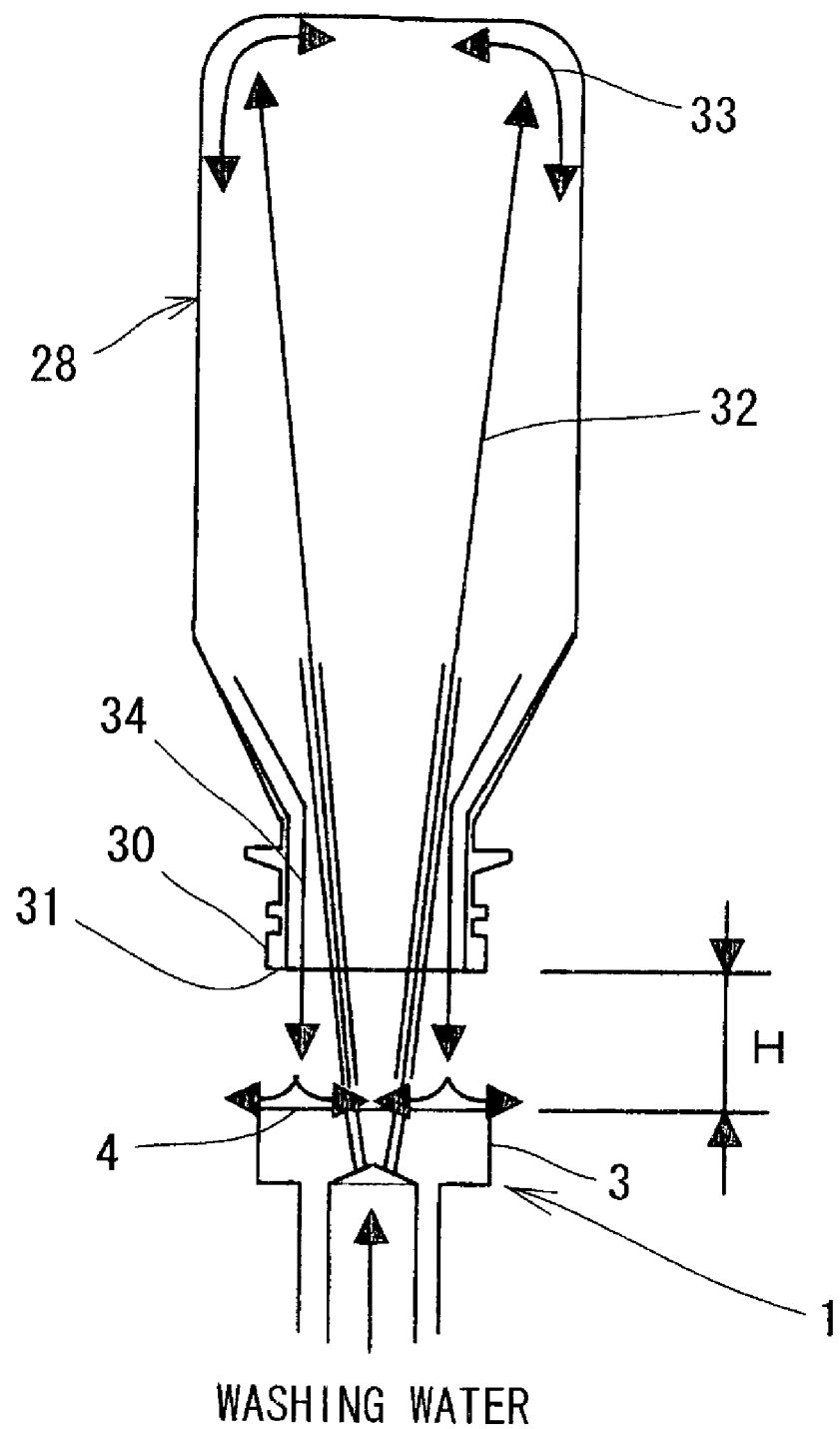
FIG. 4 is a schematic drawing illustrating the container washing state with the non-inserted nozzle shown in FIG. 1 of an embodiment of the method for sterilizing and washing a container in accordance with the present invention.

FIG. 4 illustrates an embodiment relating to the case in which the inner surface of the container is washed by using the non-inserted nozzle 1 shown in FIG. 1, but the present invention can be similarly employed in the case where the inner surface of the container is sterilized with hot water or sterilizing liquid.

The non-inserted nozzles 1 are fixedly arranged below the container holding means arranged for each pocket of a washing turret 49 and a washing turret 51 shown in FIG. 6. As shown in FIG. 4, the non-inserted nozzles are at a predetermined distance H from the lower end surface 31 of the container held with the container holding means and are fixedly disposed at a frame that rotates integrally with the turrets so that the axis center thereof matches the container axis. If the distance H is small, liquid discharge is poor, and if the distance is large, the below-described juggling effect is eliminated. Therefore, the distance H has to be set appropriately according to the type of the container. Generally, the aforementioned conditions can be satisfied when the non-inserted nozzle is disposed below the lower end surface of the mouth of the container at a distance of 5 to 50 mm, preferably 10 to 40 mm therefrom.

When the non-inserted nozzle 1 is thus arranged and the bottle is transferred through the predetermined zone in the washing process, a washing fluid (aseptic water in the case of aseptic filling) is sprayed from the non-inserted nozzle toward the bottle mouth and the inner surface is washed. The washing fluid sprayed from a plurality of inclined nozzle holes passes through the container mouth, as shown by arrows 32 and 33 in FIG. 4, falls on the corner section of the bottom part of the container, spreads over the inner surface of the bottom section and inner surface of the body wall of the container, propagates over the inner surface of the body section, becomes a cylindrical reflux liquid flow 34 and flows down from the inner peripheral surface of the mouth of the container, whereby the washing fluid comes into contact with the entire inner surface of the container and washes off the sterilizing liquid that has adhered to the inner surface of the container. The reflux liquid flow 34 that flowed down from the container falls on and spreads over the liquid-receiving surface 4 of the nozzle mouth 3 located therebelow, and is then discharged to the outside. Furthermore, because the reflux liquid that was discharged from the bottle mouth falls on the liquid-receiving surface and spreads over the liquid-receiving surface, part of the reflux liquid directed toward the inner side of the liquid-receiving surface interferes with the washing fluid sprayed from the nozzle holes and is pushed up. As a result, the sprayed fluid advances into the container in a state in which the diameter of the sprayed liquid flow is larger than that in the case of simple spraying from the nozzle holes, wetting of the container can be improved, and eventually good washing can be performed with a small quantity of washing fluid. Furthermore, the sprayed liquid flow that advances into the containers as a thickened flow interferes with part of the reflux liquid flowing down the container mouth, thereby generating the juggling effect and increasing the washing effect. Because the nozzle is a non-inserted nozzle and is not required to be inserted into the mouth of the container, the mechanism is simple and the washing process can be shortened accordingly.

Figure 5:
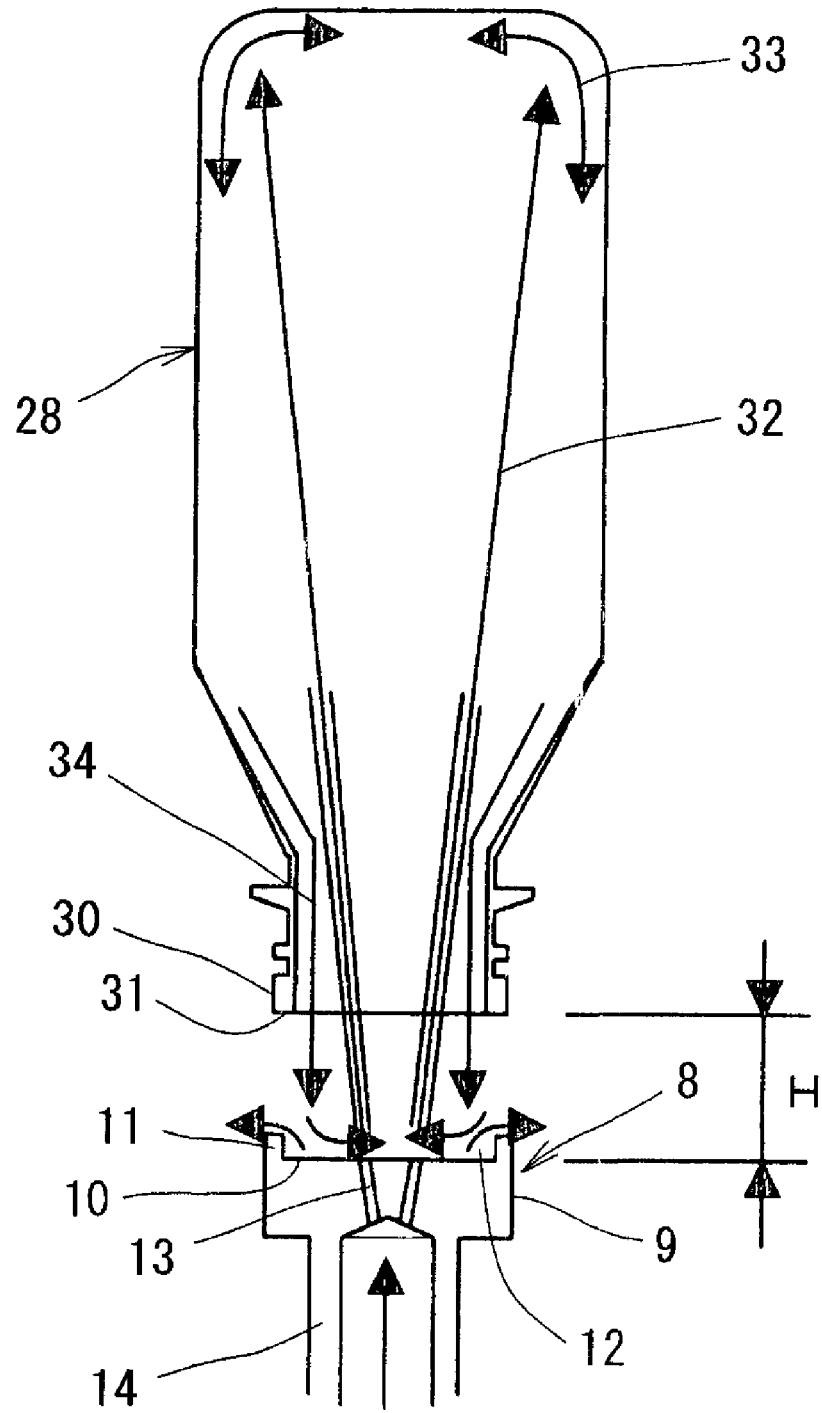
FIG. 5 is a schematic drawing illustrating the container washing state with the non-inserted nozzle shown in FIG. 2 of another embodiment of the method for sterilizing and washing a container in accordance with the present invention.

FIG. 5 shows an embodiment relating to the case where a container is washed by employing the non-inserted nozzle 8 shown in FIG. 2. In this case, because the retention recess 12 is formed in the liquid-retaining surface of the non-inserted nozzle, the juggling effect is stronger and the inner surface of the container can be washed more efficiently than in the case of the above-described embodiment. As the other actions are identical to those of the above-described embodiment, the explanation thereof is omitted.

The above-described embodiments were explained with reference to the case of employing the present invention to washing the inner surface of containers, but the sterilization of the inner surface of containers can be efficiently performed in a similar manner by employing a sterilizing fluid instead of the washing fluid. In the case of sterilization, providing tight contact of a sterilizing liquid with the inner surface of the container for a fixed interval and uniformly wetting the inner surface ensures good sterilization without leak. Accordingly, in the case of sterilization with a sterilizing liquid, by supplying air together with the sterilizing liquid into a non-inserted nozzle and jet spraying them in a mixed state of two fluids, the particles of the sterilizing liquid flow can me reduced in size, providing for tight contact with the inner surface of the container and increasing wetting thereof, the sterilizing agent can be saved, and the sterilization time can be shortened. The same effect can be also obtained during washing by using a two-fluid mixing nozzle.

FIG. 6 is a schematic view illustrating the configuration of a container sterilizing and washing apparatus for implementing the container sterilizing and washing method in accordance with the present invention. This figure illustrates a container sterilizing and washing apparatus in an aseptic loading system. The entire configuration is accommodated inside an aseptic chamber 39. The aseptic chamber is further divided into a sterilization chamber 39A and a washing chamber 39B and partitioned by a partition wall 40, except a transfer zone of the below-described sterilizing fluid discharge turret 47 and transfer turret 48. The pressure in the sterilizing chamber 39B is higher than that in the sterilizing chamber 39A and the air inside the sterilization chamber 39A does not flow into the washing chamber 39B.

In FIG. 6 illustrating this embodiment, the reference numerals 41 and 42 stand for a bottle supply turret and a bottle reversion turret, respectively. A bottle supplied in an upright state to the bottle supply turret is reversed by a well-known reversion mechanism and transferred to the bottle reversion turret when the bottle is transferred from the bottle supply turret 41 to the bottle reversion turret. The reference numeral 43 stands for a preheating turret that serves to preheat the container from the outer surface thereof to increase the sterilization efficiency. In the turret, the heated sterilizing fluid is sprayed along the bottle conveying path. The reference numerals 44 to 46 stand for sterilizing turrets. The sterilization process is divided between three turrets. The sterilizing fluid is sprayed for a different time in each sterilizing turret and the bottle is transferred to the next sterilizing turret in a state where the sterilizing fluid has adhered to the inner surface of the container. Accordingly, the sterilizing fluid adhesion state can be ensured even without spraying the sterilizing fluid therefrom and the sterilization efficiency is increased. The reference numeral 47 stands for a sterilizing fluid discharge turret and 48 is a transfer turret for transferring the sterilized bottle to a washing turret 49. The reference numerals 49, 51 stand for washing turrets in which washing nozzles for spraying aseptic water into the bottles are disposed below the turret pockets so as to perform spraying on the inner surface of bottles from below and outside the bottle mouth, similarly to the sterilizing nozzles. The reference numerals 50, 52 stand for drain turrets.

Using a combination of a large number of small-diameter turrets in the bottle sterilizing and washing apparatus of the present embodiment improves versatility of the apparatus because the sterilizing process and washing process can be divided into steps and optimum sterilizing and washing conditions can be set according to the type of the container and contents liquid that will be charged into the container by changing the spraying conditions or type of the non-contact nozzle in each process. At the same time, the installation surface area can be reduced by comparison with that where a conventional large-diameter turret was installed, and the turrets can be modularized and the combination such as the sterilizing and washing time can be easily changed according to the type of the container. For example, when the sterilizing time of the container in the sterilizing turret 44 is 4.2 sec, the sterilizing time in the sterilizing turret 45 is 1.7 sec, and the sterilizing time in the sterilizing turret 46 is 3.6 sec and the containers are transferred to a respective new turret after sterilizing, if the transfer time between the turrets is set, for example, to 0.6 sec, then spraying of the sterilizing fluid can be conducted intermittently in a sequence of spraying the sterilizing fluid onto the container for 4.2 sec, terminating the spraying for 0.6 sec, spraying for 1.7 sec, terminating the spraying for 0.6 sec, and spraying for 3.6 sec, and the inner surface of the container can be sterilized in a continuous matter. Furthermore, the washing fluid can be saved by taking washing in the washing turret 49 as a first washing step and taking washing in the washing turret 51 as a second washing step, then circulating the washing fluid used in the second washing step to the first washing step and using as the washing fluid for the first washing step.

EXAMPLE 1

Two types of nozzles, which are a non-inserted nozzle (referred to hereinbelow as "A-type nozzle") employing the nozzle mouth of the configuration shown in FIG. 1 and a non-inserted nozzle (referred to hereinbelow as "B-type nozzle") employing the nozzle mouth of the configuration shown in FIG. 2 and having a retention wall were used. The washing nozzle had four nozzle holes 6, 13 formed with a pitch of 5 mm. The inclination angle θ of the nozzle holes 6, 13 and hole diameter D were varied as shown in Table 1 and the time required to wet the entire surface of the inner wall of a bottle was measured. The bottle containers used for the test were round PET bottles with a capacity of 500 mL and angular bottles with a capacity of 2000 mL. The top surface of the socket section of the washing nozzle and bottle was set to 15 mm. The test was conducted at three flow rates: 4 L/min, 4.5 L/min, and 5 L/min. The wetting state was estimated by using red water for the washing fluid and visually evaluating the adhesion state of the red water.

The results are shown in Table 1. The case where the entire surface was wetted within a washing time of 1.5 sec with the turret group shown in FIG. 6 was considered to be the best (⊚), the case where the entire surface was wetted within 1.6 to 3 sec was considered to be good (○), and the case where more than 3.1 sec were required was considered to be poor (x). The results obtained demonstrated that with any non-inserted nozzle in accordance with the present invention, the entire surface could be wetted within at least 2 sec. When the A-type nozzle of the present embodiment was used, for a 500 mL bottle, good results were obtained at a flow rate of 4.5 L/min or more; when the B-type nozzle was used, good results were obtained at 3.5 L/min. In particular when the B-type nozzle was used, it was confirmed that the amount of saved fluid was especially high. This appears that the juggling effect was higher in the case of the B-type nozzles.

TABLE 1

| NOZZLE NUMBER | ANGLE θ (°) | NUMBER OF HOLES | HOLE DIAMETER D (mm) | LIQIOD RETAINING RECESS (mm) | DISTANCE BETWEEN BOTTLE AND NOZZLE (mm) | BOTTLE | FLOW RATE (L/min) | TIME REQUIRED TO WET THE ENTIRE SURFACE (SEC) (1) | (2) | (3) | EVALUATION* |
|---|---|---|---|---|---|---|---|---|---|---|---|
| A-1 | 2.5 | 4 | 1.5 | NONE | 15 | 500 mL, round | 4 | 6.4 | 10 or more | 10 or more | X |
|  |  |  |  |  |  |  | 4.5 | 2.7 | 2.5 | 2.3 | ○ |
|  |  |  |  |  |  |  | 5 | 1.8 | 1.5 | 1.4 | ○ |
| A-2 | 5 | 4 | 1.5 | NONE | 15 | 500 mL, round | 4 | 2.3 | 2.3 | 1.8 | ○ |
|  |  |  |  |  |  |  | 4.5 | 1.5 | 1.7 | 1.8 | ○ |
|  |  |  |  |  |  |  | 5 | 1.2 | 1.3 | 1.2 | ◎ |
| A-3 | 2.5 | 4 | 2.0 | NONE | 15 | 500 mL, round | 4 | 5.0 | 3.3 | 3.1 | X |
|  |  |  |  |  |  |  | 4.5 | 2.6 | 1.8 | 2.7 | ○ |
|  |  |  |  |  |  |  | 5 | 1.8 | 2.3 | 1.9 | ○ |
| A-4 | 5.0 | 4 | 2.0 | NONE | 15 | 500 mL, round | 4 | 3.4 | 2.5 | 1.9 | X |
|  |  |  |  |  |  |  | 4.5 | 1.6 | 1.8 | 1.9 | ○ |
|  |  |  |  |  |  |  | 5 | 1.3 | 1.2 | 1.4 | ◎ |
| B-1 | 5.0 | 4 | 1.5 | PRESENT | 15 | 500 mL, round | 3 | 2.9 | 2.8 | 3.9 | X |
|  |  |  |  |  |  |  | 3.5 | 1.9 | 1.7 | 2.1 | ○ |
|  |  |  |  |  |  |  | 4 | 1.1 | 1.5 | 1.5 | ◎ |
| B-2 | 5.0 | 4 | 2.0 | PRESENT | 15 | 500 mL, round | 3.5 | 2.2 | 2.3 | 1.9 | ○ |
|  |  |  |  |  |  |  | 4 | 1.5 | 2.2 | 1.7 | ○ |
|  |  |  |  |  |  |  | 4.5 | 1.6 | 1.2 | 1.6 | ○ |
| B-1 | 1.5 | 4 | 1.5 | PRESENT | 15 | 2000 mL, angular | 4 | 2.2 | 2.0 | 2.1 | ○ |
|  |  |  |  |  |  |  | 5 | 1.7 | 1.8 | 1.7 | ○ |
|  |  |  |  |  |  |  | 6 | 1.3 | 1.4 | 1.4 | ◎ |

*NOTE ◎: time required to wet the entire surface: within 1.5 sec ○: time required to wet the entire surface: 1.6 to 3 sec X: time required to wet the entire surface: 3.1 sec or longer

EXAMPLE 2

A liquid discharge state was studied by changing the distance in the washing test in order to study the effect of the distance H between the liquid-retaining surface of the non-inserted nozzle and the lower end surface of the container mouth. The results are shown in Table 2. The results demonstrated that the distance clearly affected the state of the liquid flowing down in this test; thus, the liquid discharge ability was poor when the distance H was less than 4 mm, and the interference with the falling reflux liquid was facilitated when the distance was 40 mm or more. In the case of this test example, it was confirmed that the appropriate distance H was 5 to 35 mm. However, the optimum distance H differs depending on the bottle mouth diameter and the range of the distance H increases with the increase in the mouth diameter.

Non-Inserted Nozzle Used: B-Type Nozzle

Four nozzle holes, inclination angle θ=5.0°, nozzle diameter D=1.5 mm, height of retention wall 4 mm. Supplied bottles: 500 mL PET bottle (mouth diameter 28 mm). Flow Rate: 4 L/min.

TABLE 2

| DISTANCE (H), mm | WASHING ABILITY | ESTIMATION |
|---|---|---|
| 4 | LIQUID DISCHARGE ABILITY IS RATHER POOR | Δ |
| 5 | GOOD | ○ |
| 10 | GOOD | ○ |
| 15 | GOOD | ○ |
| 20 | GOOD | ○ |
| 25 | GOOD | ○ |
| 30 | GOOD | ○ |
| 35 | SOME INTERFERENCE | ○ |
| 40 | INTERFERENCE | Δ |

EXAMPLE 3

In order to verify the juggling effect of the B-type nozzle provided with a retention recess on the liquid-retaining surface, the non-inserted nozzles in which the number of nozzle holes, hole diameter, and height of retention wall differed as shown in Table 3 were used, a test was conducted three times on each nozzle by changing the spraying flow rate, and the time required to wet the entire inner surface of the container was measured. The distance between the liquid-retaining surface and the top surface of bottle mouth was set to 15 mm in all cases. The supplied bottles were 500 mL round PET bottles. The results are shown in Table 3.

TABLE 3

| NOZZLE NUMBER | NUMBER OF HOLES | ANGLE θ (°) | HOLE DIAMETER D (mm) | LIQUID RETAINING RECESS (mm) | DISTANCE BETWEEN BOTTLE AND NOZZLE (mm) | BOTTLE | FLOW RATE (L/min) | TIME REQUIRED TO WET THE ENTIRE SURFACE (sec) (1) | (2) | (3) | EVALUATION* |
|---|---|---|---|---|---|---|---|---|---|---|---|
| B-3 | 4 | 5.0 | 1.5 | 2 | 15 | 500 mL, round | 3.5 | 1.6 | 2.0 | 2.2 | ○ |
|  |  |  |  |  |  |  | 4 | 1.9 | 1.8 | 1.5 | ○ |
|  |  |  |  |  |  |  | 4.5 | 1.4 | 1.2 | 1.7 | ○ |

TABLE 3-continued

| NOZZLE NUMBER | NUMBER OF HOLES | ANGLE θ (°) | HOLE DIAMETER D (mm) | LIQUID RETAINING RECESS (mm) | DISTANCE BETWEEN BOTTLE AND NOZZLE (mm) | BOTTLE | FLOW RATE (L/min) | TIME REQUIRED TO WET THE ENTIRE SURFACE (sec) (1) | (2) | (3) | EVALUATION* |
|---|---|---|---|---|---|---|---|---|---|---|---|
| B-4 | 4 | 5.0 | 1.5 | 4 | 15 | 500 mL, round | 3 | 2.6 | 3.4 | 2.4 | X |
|  |  |  |  |  |  |  | 3.5 | 1.5 | 2.1 | 1.8 | ○ |
|  |  |  |  |  |  |  | 4 | 1.1 | 1.3 | 1.1 | ◎ |
| B-5 | 6 | 5.0 | 1.2 | 4 | 15 | 500 mL, round | 4 | 1.3 | 1.5 | 2.3 | ○ |
|  |  |  |  |  |  |  | 4.5 | 1.1 | 1.1 | 1.2 | ◎ |
| B-6 | 8 | 5.0 | 1.1 | 4 | 15 | 500 mL, round | 4 | 1.7 | 1.5 | 2.2 | ○ |
|  |  |  |  |  |  |  | 4.5 | 1.1 | 1.5 | 1.3 | ◎ |

*NOTE ◎: time required to wet the entire surface: within 1.5 sec ○: time required to wet the entire surface: 1.6 to 3 sec X: time required to wet the entire surface: 3.1 sec or longer As shown in Table 3, in the case of the B-typed nozzle, the results obtained that good wetting ability could be obtained with all the nozzles and the juggling effect was good. In this embodiment, with the retention recess of 4 mm, the time required to wet the entire surface at a lower flow rate was found to be shorter than that with the retention recess of 2 mm, and a better juggling effect was apparently demonstrated with the retention recess of 4 mm.

The above-described examples confirmed that the non-inserted nozzle and sterilizing and washing method in accordance with the present invention can substantially decrease the necessary amount of washing fluid and sterilizing fluid.

INDUSTRIAL APPLICABILITY

The present invention is especially advantageous for washing the inner surface in an aseptic filling system for bottle containers, but is not limited to aseptic filling and can be used in sterilization apparatuses and washing apparatuses for containers when the containers are sterilized, washed, and filled, such as hot pack or usual normal-temperature filling. Furthermore, the present invention is applicable to containers of various shapes including round or angular bottles and also can be used for sterilizing and washing containers of various materials such as plastics, metals, and glass.

The invention claimed is:

1. A system of cleaning a container with an opening by washing or sterilizing the container by spraying a sterilizing fluid or washing fluid into the container from below a mouth of the container to sterilize or wash the container in an inverted state thereof, the system comprising:
   a non-inserted nozzle, and
   a container holder which holds the container,
   the non-inserted nozzle comprising:
   a hollow nozzle stem having a fluid channel formed inside thereof, and a nozzle mouth provided at a top section of said hollow nozzle stem,
   wherein said nozzle mouth has a liquid-receiving surface on an upper end surface, and a plurality of nozzle holes which link to the fluid channel of said nozzle stem, and are formed obliquely at a predetermined angle in a substantially central section of said liquid-receiving surface,
   wherein said liquid-receiving surface is flat so that the fluid discharged from the container during container washing or sterilizing can be retained, and a juggling effect can be generated into the fluid sprayed from the nozzle holes,
   wherein said non-inserted nozzle is positioned below the mouth of the container during said spraying of sterilization fluid or washing fluid into said container and
   wherein said nozzle mouth and said liquid receiving surface are substantially co-planar on a horizontal plane and
   wherein a diameter of the liquid-receiving surface is larger than or equal to the diameter of the mouth of the container.

2. The system according to claim 1, wherein from two to ten said nozzle holes are formed with a predetermined spacing on a circle of a substantially central section of said liquid-receiving surface, the inclination angle θ of outward spread is 1°-8°, and the nozzle hole diameter is 0.5-4.0 mm.

* * * * *